(12) United States Patent
Chen et al.

(10) Patent No.: US 11,123,072 B2
(45) Date of Patent: Sep. 21, 2021

(54) TISSUE CLOSURE DEVICE AND MEDICAL INSTRUMENT

(71) Applicant: TOUCHSTONE INTERNATIONAL MEDICAL SCIENCE CO., LTD, Suzhou (CN)

(72) Inventors: Wangdong Chen, Suzhou (CN); Kaifen Fu, Suzhou (CN); Yanping Ye, Suzhou (CN); Tuo Shu, Suzhou (CN); Laicun Li, Suzhou (CN)

(73) Assignee: TOUCHSTONE INTERNATIONAL MEDICAL SCIENCE CO., LTD., Jiangsu (CN)

( * ) Notice: Subject to any disclaimer, the term of this patent is extended or adjusted under 35 U.S.C. 154(b) by 365 days.

(21) Appl. No.: 16/311,150

(22) PCT Filed: Dec. 30, 2016

(86) PCT No.: PCT/CN2016/113460
§ 371 (c)(1),
(2) Date: Dec. 18, 2018

(87) PCT Pub. No.: WO2018/028134
PCT Pub. Date: Feb. 15, 2018

(65) Prior Publication Data
US 2020/0305877 A1 Oct. 1, 2020

(30) Foreign Application Priority Data

Aug. 8, 2016 (CN) .......................... 201610643532.6
Aug. 8, 2016 (CN) .......................... 201610645091.3
Aug. 31, 2016 (CN) .......................... 201610776877.9

(51) Int. Cl.
*A61B 17/11* (2006.01)
*A61B 17/115* (2006.01)
*A61B 17/072* (2006.01)

(52) U.S. Cl.
CPC ......... *A61B 17/1114* (2013.01); *A61B 17/115* (2013.01); *A61B 2017/07285* (2013.01); *A61B 2017/1142* (2013.01)

(58) Field of Classification Search
CPC . A61B 17/072; A61B 17/1114; A61B 17/115; A61B 2017/0046;
(Continued)

(56) References Cited

U.S. PATENT DOCUMENTS 8,960,521 B2 2/2015 Kostrzewski
2012/0241492 A1* 9/2012 Shelton, IV ..... A61B 17/00491
227/175.1
2015/0335330 A1* 11/2015 Scirica ................. A61B 17/068
227/176.1

FOREIGN PATENT DOCUMENTS

CN 201082177 Y 7/2008
CN 201279163 Y 7/2009
(Continued)

OTHER PUBLICATIONS

International Search Report for PCT/CN2016/113460 dated May 17, 2017 and its English translation provided by WIPO.
(Continued)

*Primary Examiner* — Mohamed G Gabr
(74) *Attorney, Agent, or Firm* — Ladas & Parry, LLP

(57) ABSTRACT

The present invention provides a tissue closure device, comprising: a first clamping base and a second clamping base which may be opened/closed relatively and form an accommodation cavity after being closed; and a pouch assembly which may be driven to move in the accommodation cavity, wherein: the pouch assembly comprises a staple pusher, a pair of needle heads movably connected to the staple pusher, and a connection portion connected to the proximal ends of the pair of needle heads; and when the staple pusher moves from the proximal end to the distal end, (Continued)

the pair of needle heads pushes a tubular tissue located in the accommodation cavity to the distal end until the distal ends of the pair of needle heads are closed to close the tubular tissue into a purse string. A bundled purse string with a gathered center may be formed through the tissue closure device.

15 Claims, 13 Drawing Sheets

(58) Field of Classification Search
CPC .......... A61B 2017/07214; A61B 2017/07257; A61B 2017/07278; A61B 2017/07285; A61B 2017/1142; A61B 2017/2927
See application file for complete search history.

(56) References Cited

FOREIGN PATENT DOCUMENTS

| CN | 101966093 A | 2/2011 |
|---|---|---|
| CN | 202104970 U | 1/2012 |
| CN | 203029299 U | 7/2013 |
| CN | 103619269 A | 3/2014 |
| CN | 103654898 A | 3/2014 |
| CN | 203564294 U | 4/2014 |
| CN | 203609466 U | 5/2014 |
| CN | 203634229 U | 6/2014 |
| CN | 103976769 A | 8/2014 |
| CN | 104434243 A | 3/2015 |
| CN | 105997175 A | 10/2016 |
| CN | 106073842 A | 11/2016 |
| CN | 106108968 A | 11/2016 |
| CN | 206120385 U | 4/2017 |
| CN | 206120386 U | 4/2017 |
| CN | 206381205 U | 8/2017 |
| EP | 0604789 A1 | 7/1994 |
| JP | 06142107 | 5/1994 |

OTHER PUBLICATIONS

Written Opinion of the International Search Authority for PCT/CN2016/113460 dated May 17, 2017 and its English translation provided by Google Translate.

Office Action dated Feb. 24, 2018 for Chinese Patent Application No. 201610643532.6, the search report, and its English translation by Global Dossier.

Office Action dated Dec. 5, 2017 for Chinese Patent Application No. 201610645091.3, the search report, and its English translation provided by Google Translate.

Office Action dated Mar. 8, 2018 for Chinese Patent Application No. 201610776877.9, the search report, and its English translation provided by Google Translate.

* cited by examiner

TISSUE CLOSURE DEVICE AND MEDICAL INSTRUMENT

CROSS-REFERENCE TO RELATED APPLICATIONS

The present application is the U.S. national phase of PCT/CN2016/113460 filed on Dec. 30, 2016, which claims the priority to the Chinese Patent Application No. 201610643532.6 filed on Aug. 8, 2016, the Chinese patent application No. 201610645091.3 filed on Aug. 8, 2016, and the Chinese patent application No. 201610776877.9 filed on Aug. 31, 2016, the disclosures of which are incorporated herein by reference in their entireties.

TECHNICAL FIELD

The present invention relates to the technical field of medical instruments, and more particularly, to a tissue closure device and a medical instrument having the tissue closure device.

BACKGROUND

In an existing digestive tract anastomosis surgery, a linear stapler or arcuate stapler is generally used firstly for performing multi-angle resection and anastomosis on human tubular tissues, and then connecting and anastomosis of the tubular tissues are carried out using a circular stapler.

However, after the human tubular tissues being performed resection and anastomosis with the linear stapler or arcuate stapler, a cross-staple phenomenon will appear due to linear staple lines on the anastomosis stoma, especially, due to the limitations of both a human pelvic floor operation space and the swing angle of the linear stapler when the surgery is performed at a lower rectum position. As a result, "dog ears" cannot be avoided when the circular stapler is used to perform the anastomosis of tissues. Thus, under such circumstances, the surgery has a higher risk of stoma fistula, and the surgery costs are much higher.

SUMMARY

Objects of the present invention are to provide a tissue closure device and a medical instrument having the tissue closure device.

In order to achieve the above objects, the present invention provides a tissue closure device, comprising: a first clamping base and a second clamping base which may be opened/closed relatively and form an accommodation cavity after being closed, wherein: each of the first clamping base and the second clamping base comprises a clamping housing, a clamping plate fixed in the clamping housing and a channel which is located between the clamping housing and the clamping plate and extends from a proximal end to a distal end, the clamping plate is provided with a plurality of openings which is arranged at intervals from the proximal end to the distal end and communicated with the channel and the accommodation cavity, and convex blocks which are located in the openings respectively and may get close to or apart from the clamping housing in the openings in the direction perpendicular to the clamping plate, a needle groove which penetrates through the convex block from the proximal end to the distal end and is communicated with the accommodation groove is arranged on the convex block, and the convex blocks on the clamping plates of the first clamping base and the second clamping base are staggered from the proximal end to the distal end;

a pushing block which may be driven to move from the proximal end to the distal end in each of the channels to successively drive the plurality of convex blocks on the clamping plate to move in the direction away from the clamping housing, wherein after the pushing block moves towards the distal end, the convex block located at the proximal end of the pushing block disengages from the pushing block; and a pouch assembly which may be driven to move from the proximal end to the distal end and comprise a staple pusher, a pair of needle heads movably connected to the staple pusher, and a connection portion connected to the proximal ends of the pair of needle heads, wherein when the staple pusher moves from the proximal end to the distal end, the pair of needle heads respectively moves in the needle grooves of the convex blocks on the clamping plates of the first clamping base and the second clamping base, pierces into a tubular tissue, gradually pushes the tubular tissue to the distal end and gathers the tubular tissue until the distal ends of the pair of the needle heads are closed to close the tubular tissue into a purse string.

In order to achieve the above objects, the present invention provides a medical instrument comprising an instrument body, a tissue closure device detachably connected to the distal end of the instrument body, a firing device connected onto the instrument body for firing the tissue closure device.

The present invention has the following beneficial effects: a bundled purse string with a gathered center is formed by the tissue closure device, and the risk of stoma fistula is reduced.

DETAILED DESCRIPTION

The present invention will be described in detail below with reference to specific embodiments shown in the accompanying drawings. However, these embodiments are not intended to limit the present invention, and changes of structures, methods or functions, made by an ordinary person skilled in the art according to these embodiments are included within the scope of protection of the present invention.

In order to clearly express the position and direction described in the present invention, reference is made to an instrument operator, the end close to the operator is a proximal end, and the end away from the operator is a distal end.

Figure 19:
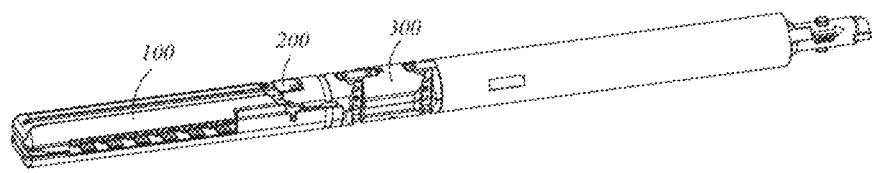
FIG. 19 is a structural diagram after the tissue closure device of the present invention cooperates with a transition connector.

As shown in FIG. 19, the medical instrument of the present invention comprises an instrument body (not shown), a tissue closure device 100 detachably connected to the distal end of the instrument body, and a firing device (not shown) connected onto the instrument body for firing the tissue closure device 100. The tissue closure device 100 further comprises a transition connector 300 connected to the instrument body. It may be understood by a person skilled in the art that specific structures of the instrument body and the firing device are not limited as long as they may cooperatively firing the tissue closure device 100. For example, the instrument body may adopt, but is not limited to, the instrument body mechanism of a linear or arcuate stapler.

As shown in FIGS. 1-19, the tissue closure device 100 of a preferred embodiment of the present invention is mainly used for anastomosis surgeries, such as a digestive tract anastomosis surgery, for resecting lesion portions of human tubular tissues.

Typical human tubular tissues comprise, but are not limited to, blood vessels including arteries and veins; digestive tracts including the esophagus, stomach, small intestine, colon and rectum; the bile duct and pancreas; the urinary tract including the ureters, bladder and urethra; the fallopian tubes; and the like. It may be understood that the tissue closure device 100 may be used to perform anastomosis on the same kind of human tubular tissue or different kinds of human tubular tissue. For example, when a lesion occurs in the middle portion of the colon, the tissue closure device 100 is used for performing anastomosis on two portions of the colon and a recreated tubular path is the colon itself. When the lesion portion is the sigmoid colon which is directly connected to the rectum, the tissue closure device 100 is used for performing anastomosis on the colon and the rectum, and a recreated tubular path is located between the colon and the rectum.

The tissue closure device 100 comprises a first clamping base 11 and a second clamping base 12 which may be opened/closed relatively. When the first clamping base 11 and the second clamping base 12 are closed, an accommodation cavity 13 is formed between the first clamping base 11 and the second clamping base 12 for clamping a human tubular tissue.

The first clamping base 11 and the second clamping base 12 may be opened relatively for allowing part of the human tubular tissue to enter the accommodation cavity 13, then the first clamping base 11 and the second clamping base 12 are closed, and thus the part of the human tubular tissue is clamped in the accommodation cavity 13 by the first clamping base 11 and the second clamping base 12 for facilitating subsequent operations. It may be understood by a person skilled in the art that the so-called subsequent operations comprise, but are not limited to: enabling the part of the human tubular tissue to form a bundled purse string with a gathered center; cutting the human tubular tissue; and the like.

In this embodiment, the proximal end of the first clamping base 11 is pivotally connected to the proximal end of the second clamping base 12, while the distal end of the first clamping base 11 and the distal end of the second clamping base 12 are separated structures, so that the accommodation cavity 13 could be opened or closed. When the distal end of the first clamping base 11 and the distal end of the second clamping base 12 are separated from each other, the first clamping base 11 and the second clamping base 12 form an approximately V-shaped opening.

To be specific, each of the first clamping base 11 and the second clamping base 12 comprises a groove-shaped clamping housing 14, at least one clamping plate 15 fixed in the clamping housing 14, and a channel 16 which is formed by the clamping housing 14 and the at least one clamping plate 15 located in the clamping housing 14 and extends from the proximal end to the distal end. In the embodiment shown in FIGS. 1-19, each of the first clamping base 11 and the second clamping base 12 is provided with two clamping plates 15. In other embodiments, each of the first clamping base 11 and the second clamping base 12 may also comprise one clamping plate 15. Alternatively, the first clamping base 11 and the second clamping base 12 may also be free of clamping plate 15.

The clamping housing 14 and the clamping plate 15 are arranged separately, and the combinations thereof may adopt, but are not limited to, the following two ways: as shown in FIGS. 1-8, a plurality of fixing columns 141 is arranged on one of the clamping housing 14 and the clamping plate 15, fixing grooves 142 which are in one-to-one correspondence with the fixing columns 141 are arranged on the other one of the clamping housing and the clamping plate, and the clamping housing 14 is fixed to the clamping plate 15 through the fixing columns 141 and the fixing grooves 142; or as shown in FIGS. 9-15, a pin hole 141' is arranged on the clamping housing 14, and the clamping housing 14 is fixed to the clamping plate 15 through a pin. After the clamping housing 14 and the clamping plate 15 are fixed together, the clamping housing 14 and the clamping plate 15 define the channel 16 which extends from the proximal end to the distal end, Of course, the clamping housing 14 and the clamping plate 15 may also be arranged integrally.

A pivot shaft 143 is arranged at the proximal end of the clamping housing 14 of the first clamping base 11, A pivot shaft hole 144 cooperating with the pivot shaft 143 is arranged at a position, close to the proximal end, of the clamping housing 14 of the second clamping base 12. When the pivot shaft 143 is inserted into the pivot shaft hole 144 and the first clamping base 11 and the second clamping base 12 are closed, the distal ends of the first clamping base 11 and the second clamping base 12 are flushed with each other, and the proximal end of the clamping housing 14 of the second clamping base 12 exceeds the proximal end of the clamping housing 14 of the first clamping base 11 for facilitating the assembly with other instrument structures.

The clamping plate 15 is provided with a plurality of openings 17 which is arranged at intervals from the proximal end to the distal end and communicated with the channel 16 and the accommodation cavity 13, and convex blocks 18 which are located in the openings 17 respectively and may get close to or apart from the clamping housing 14 in the openings 17. It may be understood by a person skilled in the art that the plurality of openings 17 arranged at intervals may be a plurality of independent openings 17 arranged at intervals, and may also be communicated from the proximal end to the distal end to form a large opening.

At least one directional column 171 is arranged on one of the opening 17 and the convex block 18, and a directional groove 181 matched with the directional column 171 is arranged on the other one of the opening 17 and the convex block 18. The directional column 171 cooperates with the directional groove 181 to guide the convex block 18 to move close to or away from the clamping housing 14. It may also be understood that when the convex block 18 is close to or away from the clamping housing 14, the directional column 171 moves in the directional groove 181 to prevent the convex block 18 from inclination and rotation during movement. In this embodiment, two directional grooves 181 which are opposite are arranged on the convex block 18. Two directional columns 171 are arranged on an inner wall of the opening 17.

The plurality of convex blocks 18 on the same clamping plate 15 is arranged linearly. A needle groove 182 which penetrates through the convex block 18 from the proximal end to the distal end and is communicated with the accommodation groove 13 is arranged on each of the convex blocks 18. A first buckling block 151 protruding towards the second clamping base 12 is arranged at the distal end of the clamping plate 15 of the first clamping base 11. A first staple forming groove 1511 corresponding to the needle groove 182 of the convex block 18 on the clamping plate 15 of the first clamping base 11 is arranged on the first buckling block 151. A second buckling block 152 protruding towards the first clamping base 11 is arranged at the distal end of the clamping plate 15 of the second clamping base 12. A second staple forming groove 1521 corresponding to the needle groove 182 of the convex block 18 on the clamping plate 15 of the second clamping base 12 is arranged on the second buckling block 152.

It may be understood by a person skilled in the art that the first staple forming groove 1511 is located at the projection of the needle groove 182 of the convex block 18 of the first clamping base 11 on the first buckling block 151 from the proximal end to the distal end. The second staple forming groove 1521 is located at the projection of the needle groove 182 of the convex block 18 of the second clamping base 12 on the second buckling block 152 from the proximal end to the distal end.

Figure 1:
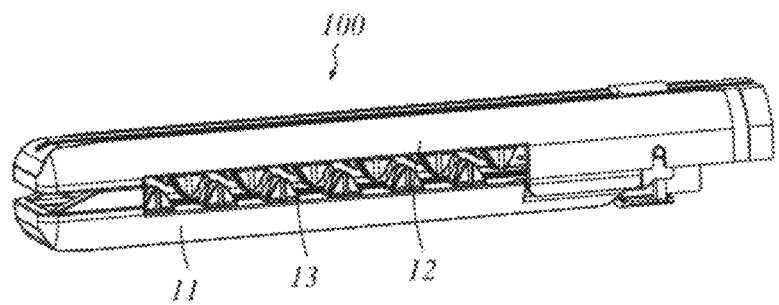
FIG. 1 is a structural diagram of the tissue closure device of the present invention.
Figure 2:
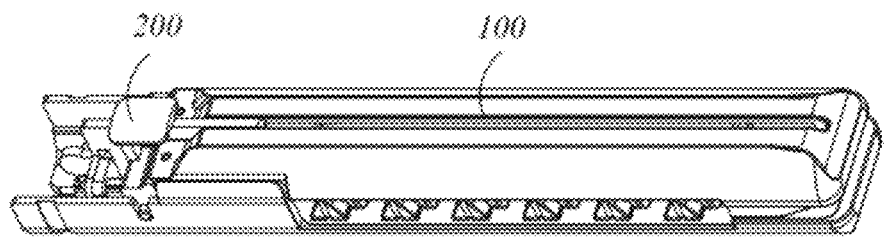
FIG. 2 is a structural diagram of the tissue closure device shown in FIG. 1 from another perspective.
Figure 3:
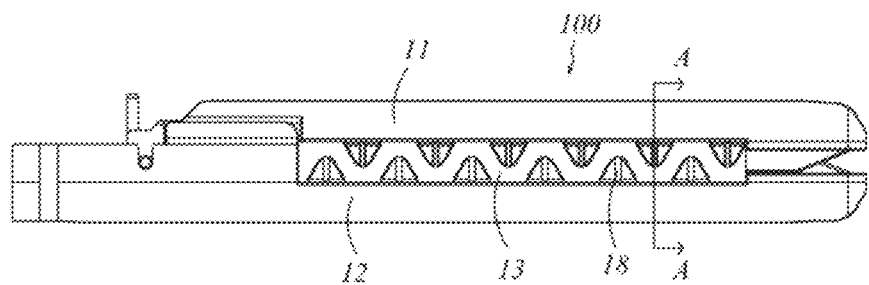
FIG. 3 is a structural diagram of the tissue closure device shown in FIG. 1 from another perspective.
Figure 4:
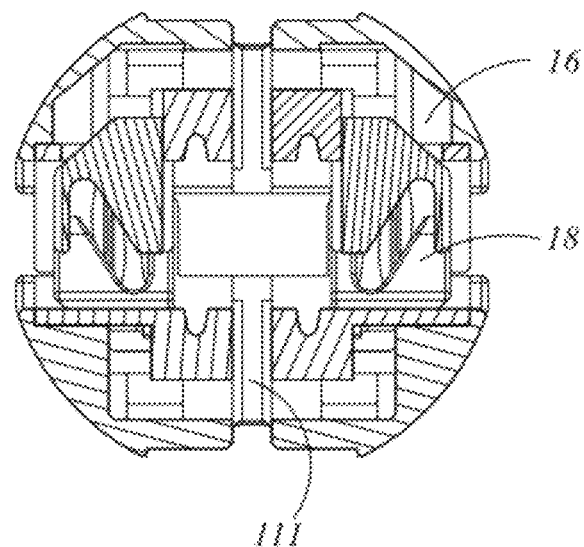
FIG. 4 is a sectional view of the tissue closure device shown in FIG. 3 along the A-A direction.
Figure 5:
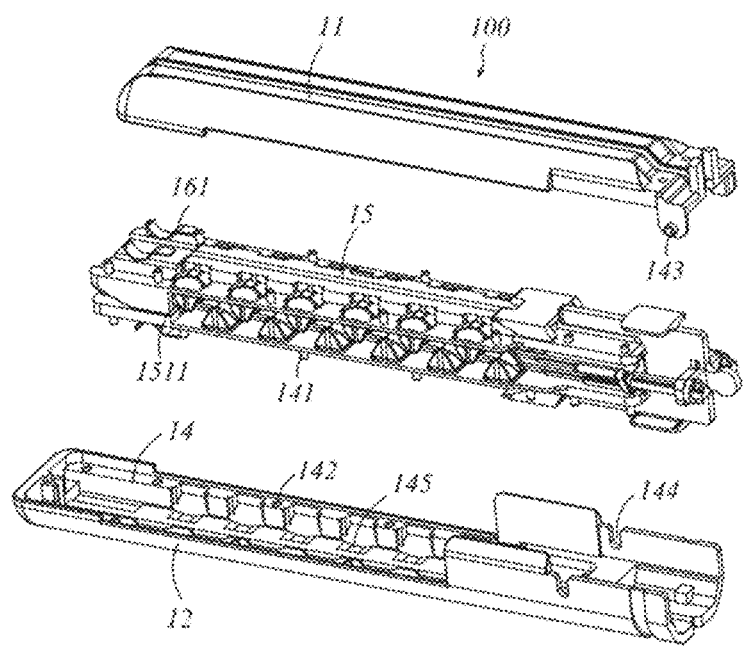
FIG. 5 is a partial exploded view of the tissue closure device shown in FIG. 1.
Figure 6:
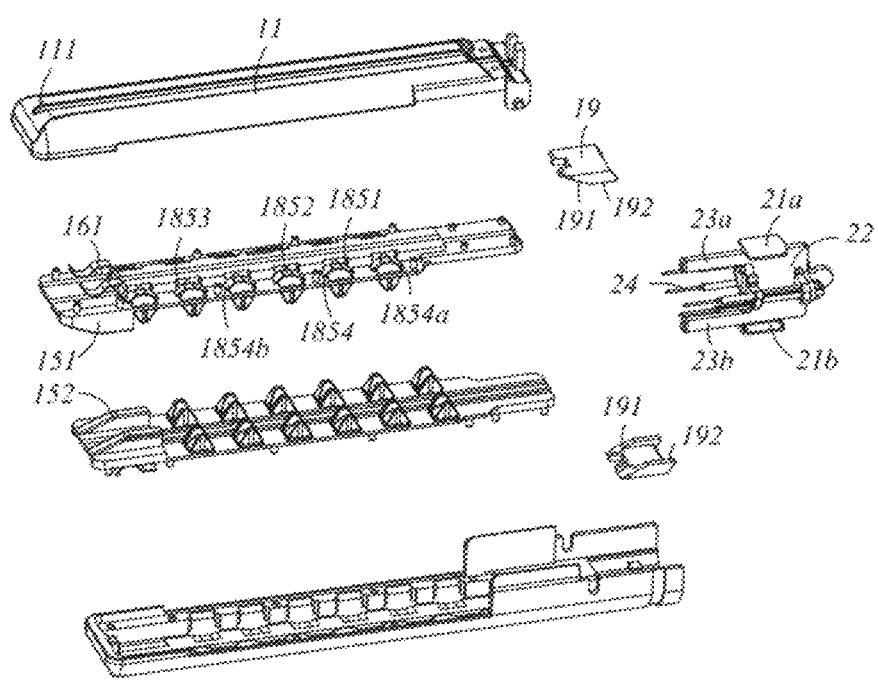
FIG. 6 is another partial exploded view of the tissue closure device shown in FIG. 1.
Figure 7:
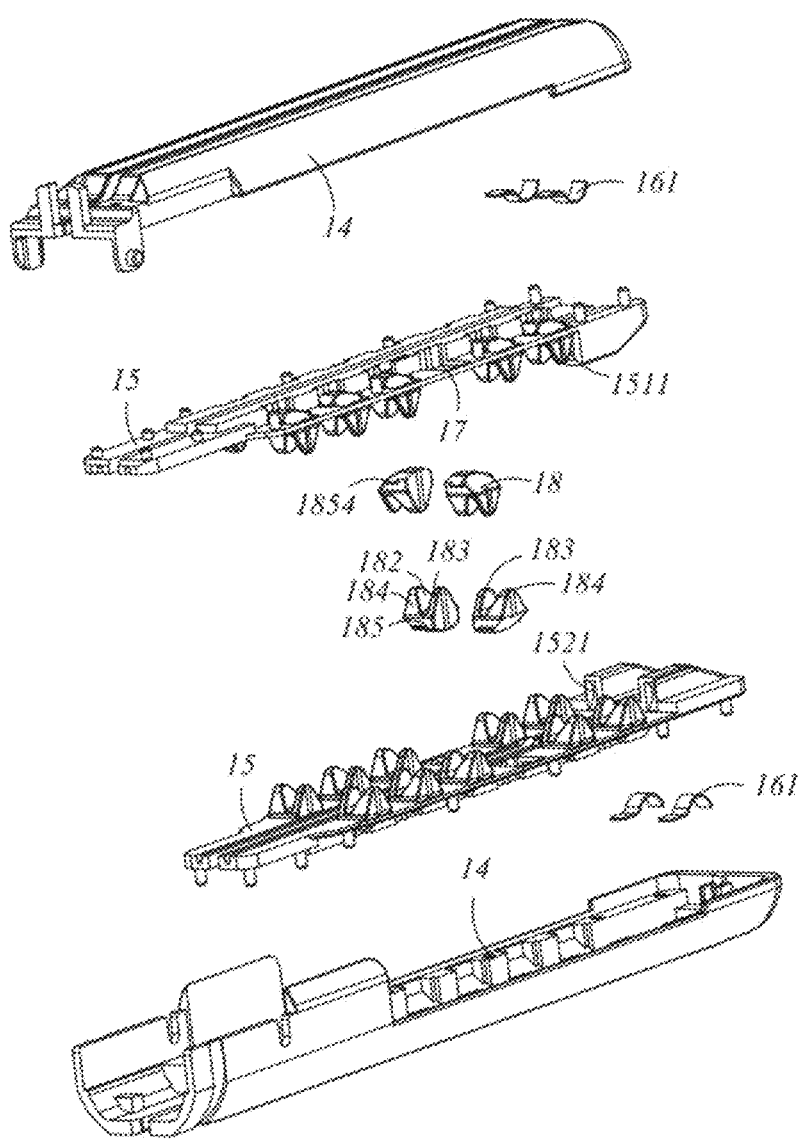
FIG. 7 is still another partial exploded view of the tissue closure device shown in FIG. 1.
Figure 8:
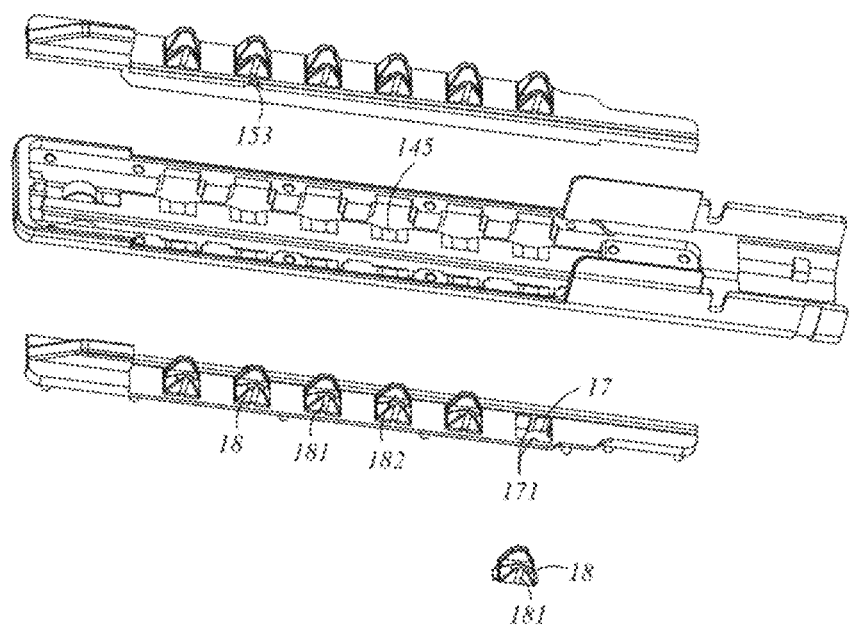
FIG. 8 is a partial exploded view of the first clamping base shown in FIG. 1.
Figure 9:
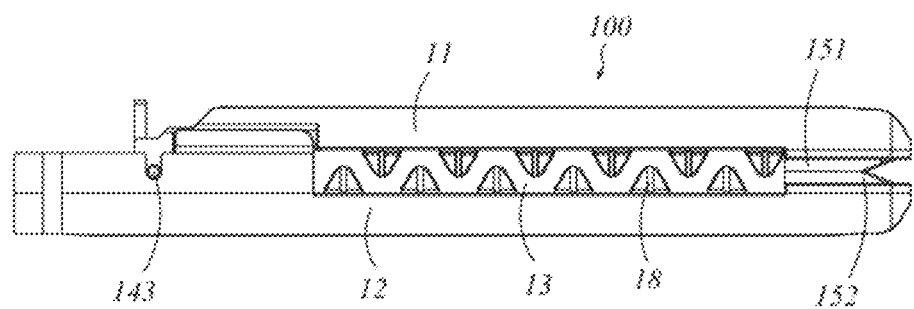
FIG. 9 is a structural diagram of the tissue closure device in another embodiment of the present invention after the first clamping base and the second clamping base cooperates with each other.
Figure 10:
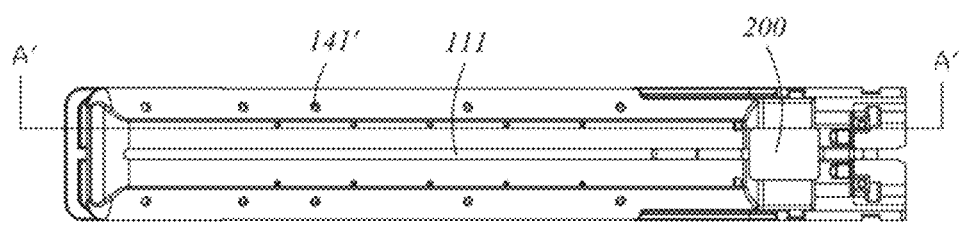
FIG. 10 is a diagram of the tissue closure device shown in FIG. 9 when the first clamping base and the second clamping base are in an open state.
Figure 11:
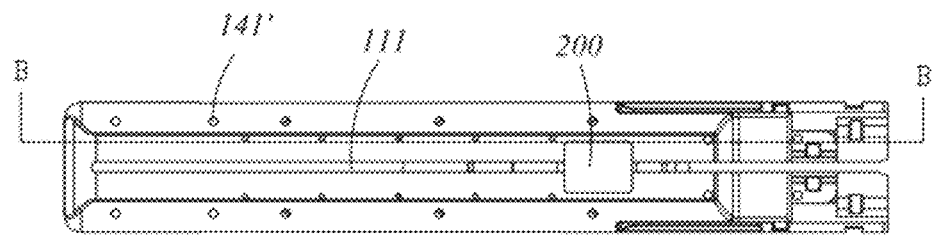
FIG. 11 is a diagram of the tissue closure device shown in FIG. 10 in a firing state.
Figure 12:
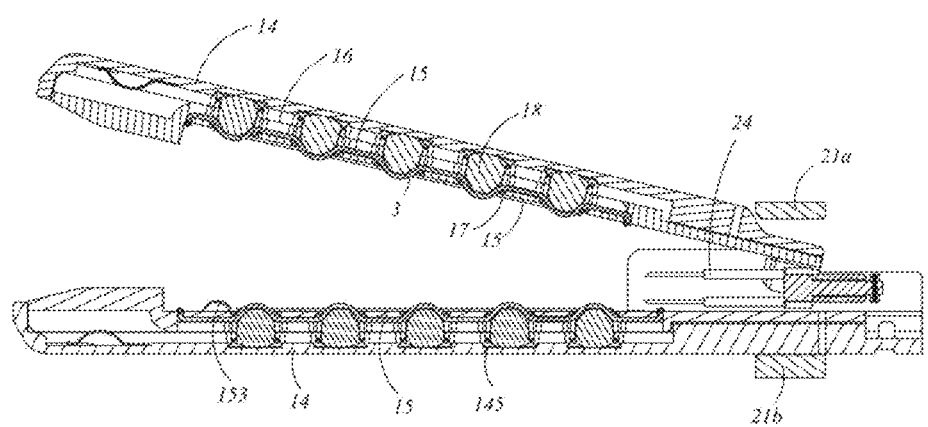
FIG. 12 is a perspective view of the tissue closure device shown in FIG. 10 along the A'-A' direction.
Figure 13:
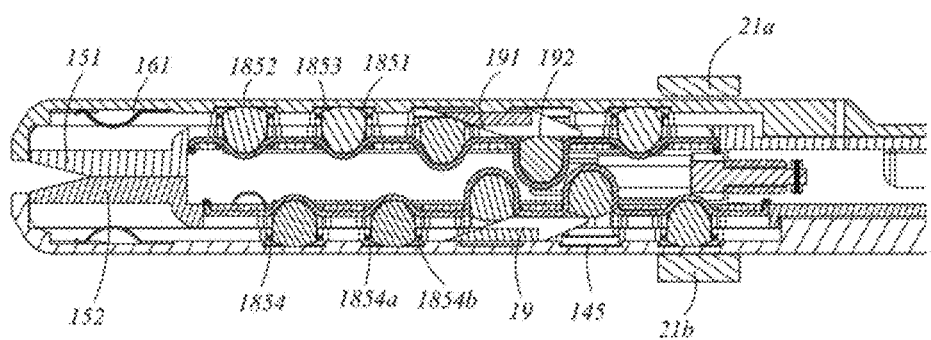
FIG. 13 is a perspective view of the tissue closure device shown in FIG. 11 along the B-B direction.
Figure 14:
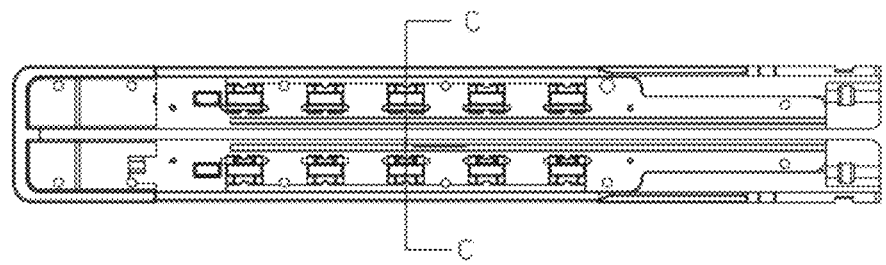
FIG. 14 is a structural diagram of the tissue closure device shown in FIG. 9 from another perspective.
Figure 15:
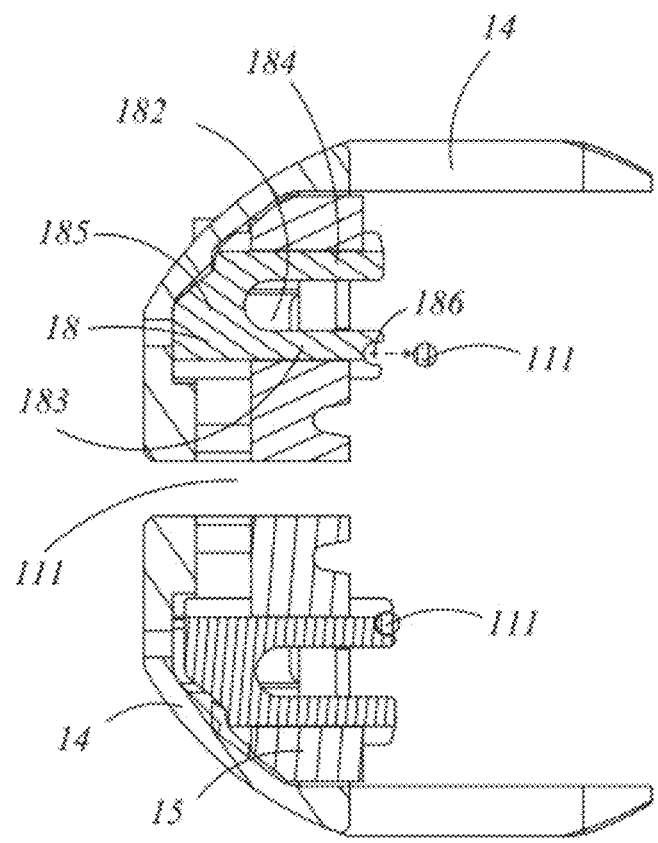
FIG. 15 is an exploded view of the first clamping base shown in FIG. 14 in the C-C direction.

In addition, when the first buckling block 151 is separated from the second buckling block 152, the human tubular tissue may enter the accommodation cavity 13 from the V-shaped opening. The first clamping base 11 and the second clamping base 12 are closed relatively by means of an instrument or manual operation until the first buckling block 151 and the second buckling block 152 close the accommodation cavity 13. Moreover, the first buckling block 151 and the second buckling block 152, as shown in FIGS. 1.8, are abutted against the second clamping base 12 and the first clamping base 11 respectively, or the first buckling block 151 and the second buckling block 152, as shown in FIGS. 9-15, are abutted against each other to achieve the effects of limiting continuous closure of the first clamping base and the second clamping base and at the same time preventing the human tubular tissue from escape.

When the first clamping base 11 and the second clamping base 12 are closed relatively, the clamping plate 15 in the first clamping base 11 is parallel to the clamping plate 15 in the second clamping base 12, and the convex blocks 18 on the first clamping base 11 and the second clamping base 12 are staggered from the proximal end to the distal end. When the first clamping base 11 and the second clamping base 12 are closed, and before the device being fired, due to the acting force of the tissue, the plurality of convex blocks 18 on the first clamping base 11 and the second clamping base 12 are respectively hidden in the channels 16 formed by the first clamping base 11 and the clamping plate 15 as well as the second clamping base 12 and the clamping plate 15. The term "parallel" refers to substantially parallel and does not specifically refer to the parallel of two planes in the strict sense. For example, a reverse jaw may be formed in the direction from the proximal end to the distal end of which the distal jaw is greater than the proximal jaw, so as to reduce the firing force.

To be specific, the convex block 18 comprises a first wall 183 and a second wall 184 which are opposite and arranged at an interval, and a connection wall 185 connected to the first wall 183 and the second wall 184, The first wall 183, the second wall 184 and the connection wall 185 define a V-shaped needle groove 182 which is open towards the side away from the connection wall 185.

The proximal end of an outer wall surface, away from the needle groove 182, of the connection wall 185 is provided with an inclined plane 1851 for facilitating driving, from the proximal end of the convex block 18, the convex block 18 to move away from the clamping housing 14. Further, the outer wall surface of the connection wall 185 is further provided with a plane 1852 located at the distal end of the inclined plane 1851 and a symmetrical inclined plane 1853 which is located at the distal end of the plane 1852 and symmetrical to the inclined plane 1851, such that the proximal end and the distal end of the convex block 18 may be reversely mounted. The convex block 18 can be driven, from the proximal end, to move away from the clamping housing 14 no matter whether the proximal end and the distal end of the convex block are reversely mounted. Of course, the inclined plane 1851, the plane 1852 and the symmetrical inclined plane 1853 may also form an arcuate surface together to achieve the same effect.

At least one limiting, sheet 1854 protruding outwards from one side of the connection wall 185 is arranged on the connection wall 185. When the convex block 18 moves away from the clamping housing 14, the limiting sheet 1854 is rested on the edge of the opening 17 to achieve the effect of limiting the continuous movement of the convex block, so that the outer wall surface of the connection wall 185 is located in the channel 16 all the time. In this embodiment, the connection wall 185 is provided with a distal-end limiting sheet 1854*a* and a proximal-end limiting sheet 1854*b* which extend towards two ends from the distal end and the proximal end respectively. When the convex block 18 moves away from the clamping housing 14, the distal-end limiting sheet 1854*a* and the proximal-end limiting sheet 1854b are rested on the edge of the opening 17 to achieve the effect of limiting the continuous movement of the convex block.

In addition, a limiting groove 145 for accommodating and limiting the outer wall surface of the connection wall 185 is arranged on the clamping housing 14, When the convex block 18 moves towards the clamping housing 14, the limiting groove 145 is abutted against the connection wall 185 to achieve the effect of limiting the continuous movement of the convex block, so that the ends, away from the connection wall 185, of the first wall 183 and the second wall 184 are located in the accommodation cavity 13 all the time. When the convex block 18 gets close to the clamping housing 14, the distal-end limiting sheet 1854a and the proximal-end limiting sheet 1854b are located outside the limiting groove 145.

At least one directional groove 181 is arranged on each of the outer wall surface, away from the needle groove 182, of the first wall 183 and the outer wall surface, away from the needle groove 182, of the second wall 184. A directional column 171 cooperating with the directional column 181 is provided in the opening 17. When the convex block 18 gets close to or apart from the clamping housing 14, the directional column 171 moves in the directional groove 181 to guarantee that the convex block 18 moves in the direction perpendicular to the clamping plate 15, thereby preventing the convex block 18 from inclination during movement.

To be specific, the convex block 18 may adopt the structures in the embodiments shown in FIGS. 1-8; an inner wall surface of the first wall 183 which is located in the needle groove 182, is parallel to the outer wall surface of the first wall which is away from the needle groove 182; the outer wall surface of the second wall 184 which is away from the needle groove 182, is parallel to the outer wall surface of the first wall 183; and an inner wall surface of the second wall 184 which is located in the needle groove 182, is gradually inclined, from the connection wall 185 to the side away from the connection wall 185, and towards the direction away from the first wall 183. It may also be understood that the outer wall surface of the first wall 183 which is away from the needle groove 182, is parallel to the outer wall surface of the second wall 184 which is away from the needle groove 182. The first wall 183 is uniform in thickness, while the side of the second wall 184 which is close to the connection wall 185, is thicker than the side away from the connection wall 185.

Along the direction perpendicular to the clamping plate 15, the first wall 183 of the convex block 18 on the first clamping base 11 is opposite to the second wall 184 of the convex block 18 on the second clamping base 12, and the second wall 184 of the convex block 18 on the first clamping base 11 is opposite to the first wall 183 of the convex block 18 on the second clamping base 12. It may also be understood that the direction in which the first wall 183 of the convex block 18 on the first clamping base 11 points to the second wall 184 is opposite to the direction in which the first wall 183 of the convex block 18 on the second clamping base 12 points to the second wall 184. At this time, the portions, close to the connection wall 185, of the needle grooves 182 of the plurality of convex blocks 18 of the first clamping base 11 are located on the same straight line, while the portions, close to the connection wall 185, of the needle grooves 182 of the plurality of convex blocks 18 of the second clamping base 12 are located on another straight line. Two projections of the two straight lines on the clamping plates 15 respectively in the direction perpendicular to the clamping plate 15 are arranged at an interval in the width direction of the clamping plate 15.

Accordingly, the first buckling block 151 and the second buckling block 152 are staggered in the width direction of the first clamping base 11. The first buckling block 151 is close to the first wall 183 of the convex block 18 on the first clamping base 11. The second buckling block 152 is close to the first wall 183 of the convex block 18 on the second clamping base 12. Thus, part of a thimble moving in the needle groove 182 of the first clamping base 11 and part of a thimble moving in the needle groove 182 of the second clamping base 12 are bent in different planes. Therefore, a tip-to-tip situation may be avoided, and the formed purse string is firmer, facilitating the use of the circular stapler later. Moreover, the situation that the instrument is too large in overall dimension and thus brings more injuries to the patient due to too large design staple crown of a staple caused by the fact that the projections of the needle groove 182 of the first clamping base 11 and the needle groove 182 of the second clamping base 12 on the clamping plate 15 coincide may also be avoided. In addition, the first buckling block 151 and the second buckling block 152 are staggered in the width direction of the first clamping base 11. Therefore, when the first clamping base 11 and the second clamping base 12 are closed, the first buckling block 151 and the second buckling block 152 are abutted against the first clamping base 11 and the second clamping base 12 respectively.

The convex block 18 may also adopt the structures in the embodiments shown in FIGS. 9-15: the first wall 183 and the second wall 184 are arranged in parallel and are uniform in thickness. Along the direction perpendicular to the clamping plate 15, the needle groove 182 of the first clamping base 11 and the needle groove 182 of the second clamping base 12 are located in same plane. Accordingly, the first buckling block 151 and the second buckling block 152 are arranged oppositely. Therefore, when the first clamping base 11 and the second clamping base 12 are closed, the first buckling block 151 and the second buckling block 152 are abutted against each other oppositely.

Further, the tissue closure device 100 further comprises a pushing block 19 which may be driven to move in each of the channels 16 from the proximal end to the distal end so as to successively drive the plurality of convex blocks 18 on the clamping plate 15 to move away from the clamping housing 14. After the pushing block 19 moves towards the distal end, the convex block 18 located at the proximal end of the pushing block 19 disengages from the pushing block 19, so that the convex block 18 may return to the channel 16, thereby facilitating the movement of other structures.

To be specific, the side of each of the convex block 18, facing the clamping housing 14, is provided with an inclined plane 1851 located at the proximal end and a plane 1852 located at the distal end of the inclined plane 1851. The pushing block 19 is provided with an inclined plane portion 191 which is located at the distal end and cooperates with the inclined plane 1851 and a plane portion 192 located at the proximal end of the inclined plane portion 191. When the pushing block 19 moves from the proximal end to the distal end in the channel 16, the inclined plane portion 191 acts on the inclined plane 1851 to drive the convex block 18 to move away from the clamping housing 14 until the plane 1852 is abutted against the plane portion 192. At this time, the limiting sheet 1854 is rested on the edge of the opening 17. In this embodiment, the length of the plane portion 192 along the direction extending from the proximal end to the distal end is designed as follows: when the plane portion 192 of the pushing block 19 located on the first clamping base 11 is abutted against the plane 1852 of one of the convex blocks 18, the plane portion 192 of the pushing block 19 located on the second clamping base 12 is also abutted against the plane 1852 of one of the convex blocks 18, and these two convex blocks 18 are adjacent.

Further, the tissue closure device 100 further comprises an elastic sheet 161 located at the distal end of each of the channels 16 to drive the pushing block 19 to move away from the clamping housing 14. To be specific, the elastic sheet 161 is located at the distal ends of all the convex blocks 18 on the clamping plate 15. When the pushing block 19 pushes all the convex blocks 18 to move away from the clamping base, the elastic sheet 161 drives the pushing block 19 to move away from the clamping housing 14, so that the channel 16 is not occupied, thereby facilitating the operation of other instruments.

In an embodiment where two clamping plates 15 are arranged in the clamping housing 14 of the first clamping base 11 at an interval in the width direction thereof and two clamping plates 15 are arranged in the clamping housing 14 of the second clamping base 12 at an interval in the width direction thereof, each of the first clamping base 11 and the second clamping base 12 is provided with a groove channel 111 penetrating along the direction perpendicular to the clamping plate 15 and extending from the proximal end to the distal end. The two clamping plates 15 in the first clamping base 11 are arranged at two sides of the groove channel 111 respectively along the width direction thereof. The two clamping plates 15 in the second clamping base 12 are arranged at two sides of the groove channel 111 respectively along the width direction thereof.

The tissue closure device 100 in this embodiment may form two purse strings simultaneously at one side of a tubular tissue having a lesion. For this reason, when a human tubular tissue is cut between the two purse strings, the ends of the tubular tissue having a lesion are also tied and closed by the purse strings and are not easy to disengage, thereby facilitating taking them out of the body later. But in an embodiment where only one clamping plate 15 is arranged in the first clamping base 11, the tissue closure device 100 may also form two purse strings at one side of the tubular tissue having a lesion by operation twice.

By taking the two clamping plates 15 in the first clamping base 11 as an example, the two clamping plates 15 in the same clamping base 11 may be arranged symmetrically as shown in FIGS. 1-18 and may also be arranged in parallel in the same way. In these two cases, the plurality of convex blocks 18 on the two clamping plates 15 is arranged synchronously from the proximal end to the distal end. Of course, the convex blocks 18 on the two clamping plates 15 may also be arranged non-synchronously, for example, being arranged in a staggered manner.

Compared to an embodiment where only one clamping plate 15 is arranged in the first clamping base 11, the pushing block 19 is also provided with an inclined plane portion 191 which is located at the distal end and cooperates with the inclined plane 1851 and a plane portion 192 located at the proximal end of the inclined plane portion 191. The differences are that the width of the pushing block 19 is increased, and the pushing block 19 may act on the convex blocks 18 on the two clamping plates 15 simultaneously when moving from the proximal end to the distal end in the channel 16, so as enable the corresponding convex block 18 to move away from the clamping housing 14.

Of course, the tissue closure device 100 may also comprise a pushing block 19 which may be driven to move in the channel 16 between each of the clamping plates 15 and the clamping housing 14 from the proximal end to the distal end so as to drive the convex blocks 18 on the clamping plate 15 to move away from the clamping housing 14. During use, two pushing blocks 19 are driven to move from the proximal end to the distal end simultaneously. The specific structure and movement mode of the pushing block 19 are the same as those of the above embodiment and thus will not be described here.

To be specific, the width of the plane portion 192 in the direction from the proximal end to the distal end is greater than the width of the convex block 18 in the direction from the proximal end to the distal end, so that during firing, it can be ensured that at least two of the convex blocks 18 are pushed up simultaneously, and form a wave-shaped tissue closure surface with the pushed-up opposite convex blocks 18, so as to ensure that a run-through needle groove channel may be formed in the tissue clamped by the convex blocks 18 under the action of the pushing block 19. When the pushing block 19 continues to move towards the distal end, the convex block 18 located at the proximal end of the pushing block 19 returns because of losing the action of the pushing block, thereby not hindering other mechanisms from moving towards the distal end.

To be specific, taking the two clamping plates 15 being arranged symmetrically in the first clamping base 11 as an example, when the pushing block 19 moves from the proximal end to the distal end in the channel 16 of the first clamping base 11, the inclined plane portion 191 may act on the two convex blocks 18 respectively located on the two clamping plates 15 simultaneously, so that the two convex blocks 18 move away from the clamping base.

Further, the tissue closure device 100 further comprises an elastic return mechanism 3. Along the direction perpendicular to the clamping plate 15, two ends of the elastic return mechanism 3 are cooperatively connected to the convex block 18 and the clamping plate 15 respectively. When the pushing block 19 drives the elastic return mechanism 3 to move away from the clamping housing 14, the elastic return mechanism 3 elastically deforms. When the convex block 18 disengages from the pushing block 19, the elastic return mechanism 3 acts on the convex block 18 to enable the convex block 18 to be located in the channel 16. "Two ends of the elastic return mechanism 3 are cooperatively connected to the convex block 18 and the clamping plate 15 respectively" refers to that when the convex block 18 moves away from or towards the clamping housing 14, the distance between two ends of the elastic return mechanism 3 is changed, so that the elastic return mechanism 3 elastically deforms. "Connected" may refer to being fixedly connected and may also refer to being movably abutted.

For example, one end of the elastic return mechanism 3 is connected to the side, away from the clamping housing 14, of the convex block 18, and the other end thereof is connected onto the clamping plate 15. When the elastic return mechanism 3 is in a first state, the convex block 18 is hidden in the channel 16 under the acting force of the elastic return mechanism 3. When the pushing block 19 drives the convex block 18 to move away from the clamping housing 14, the convex block 18 acts on the elastic retracing mechanism 3 to be in a second state while tightly pressing the tissue. After the convex block 18 disengages from the pushing block 19, the elastic return mechanism 3 is changed from the second state to the first state and drives the convex block 18 to move towards the clamping housing 14 until the convex block 18 returns into the channel 16.

"Connected" in "one end of the elastic return mechanism 3 is connected to the side, away from the clamping housing 14, of the convex block 18, and the other end thereof is connected onto the clamping plate 14" may refer to being fixedly connected and may also refer to being movably abutted. In addition, "the side, away from the clamping housing 14, of the convex block 18" does not specifically refer to the side, away from and substantially parallel to the clamping housing 14, of the convex block 18, but generally refers to the side, which does not directly face the clamping housing 14, of the convex block 18, comprising two sides thereof facing the distal end or the proximal end, as long as the switching of the elastic return mechanism 3 between the first state and the second state may be achieved.

In this embodiment, a line groove 186 extending from the proximal end to the distal end is arranged at the side, away from the clamping housing 14, of the first wall 183. The elastic return mechanism 3 is an elastic line. One end of the elastic line is fixed to the proximal end of the clamping plate 15, and the other end thereof extends from the proximal end to the distal end in the channel 16, successively passes through the line grooves 186 of the convex blocks 18, and then is fixed to the distal end of the clamping plate 15, Portions, located at the proximal end and the distal end of each of the convex blocks 18, of the elastic line are all located in the channel 16 and bonded to the clamping plate 15.

When the first clamping housing 11 and the second clamping housing 12 are in an original state when being opened, the elastic line is in the first state. At this time, the elastic line has a relatively small elastic deformation and the convex blocks 18 are all hidden in the channel 16 under the pressure of the elastic line. In a firing process, the pushing block 19 drives the convex block 18 to move away from the clamping housing 14 and protrude into the accommodation cavity 13, the elastic line has a relatively large elastic deformation under a larger pressure because of being pushed up by the convex block 18 and wraps the convex block 18, and portions, at the distal end and the proximal end of the convex block 18, of the elastic line are tightly bonded to the side, located in the channel 16, of the clamping plate 15. At this time, the tissue in the accommodation cavity 13 is wave-shaped. When the pushing block 19 moves towards the distal end until disengaging from the convex block 18, the convex block 18 returns into the channel 16 under the action of the contraction force of the elastic line to make space in the accommodation cavity 13.

Of course, the elastic return mechanism 3 may also comprise a plurality of elastic sub-lines cooperating with the convex blocks 18 respectively. Two ends of each of the elastic sub-lines are fixed to the clamping plates 15 located at the proximal end and the distal end of the convex block 18 respectively. The middle portion of the elastic sub-line is located in the line groove 186 to achieve the above effect.

Further, the tissue closure device 100 further comprises two elastic sheets 161 located at the distal ends of the channels 16 respectively to drive the pushing block 19 to move away from the clamping housing 14. To be specific, each of the elastic sheets 161 is located at the distal ends of all the convex blocks 18 on one clamping plate 15. When the pushing block 19 pushes all the convex blocks 18 to move away from the clamping base, the two elastic sheets 161 together drive the pushing block 19 to move away from the clamping housing 14, so that the channel 16 is not occupied, thereby facilitating the operation of other instruments.

The tissue closure device 100 further comprises a closer 200 for closing the first clamping base 11 and the second clamping base 12. The closer 200 comprises a first closure sheet 21a located at the side of the first clamping base 11 which is away from the second clamping base 12, a second closure sheet 21b located at the side of the second clamping base 12 which is away from the first clamping base 11, and a connection sheet 22 connected to the first closure sheet 21a and the second closure sheet 21b. Each of the first clamping base 11 and the second clamping base 12 is provided with a closure groove channel 111 for allowing the connection sheet 22 to move from the proximal end to the distal end. The closer 200 may be used cooperatively with the embodiments shown in FIGS. 1-8 and may also be used cooperatively with embodiments shown in FIGS. 9-15.

Since the first clamping base 11 is shorter than the second clamping base 12, when the second closure sheet 21b is located at the side, close to the proximal end, of the pivot shaft hole 144 on the second clamping base 12, the first closure sheet 21a is located at the side, facing the proximal end, of the first clamping base 11. At this time, the first clamping base 11 and the second clamping base 12 may be opened. After part of the human tubular tissue enters the accommodation cavity 13, the closer 200 is pushed to move from the proximal end to the distal end by means of an instrument or manual operation. The first closure sheet 21a and the second closure sheet 21b act on the first clamping base 11 and the second clamping base 12 respectively to close the accommodation cavity 13 and clamp the part of the human tubular tissue in the accommodation cavity 13.

In an embodiment where one clamping plate 15 is arranged in each of the first clamping base 11 and the second clamping base 12, the first closure sheet 21a and the second closure sheet 21b protrude from two opposite ends of the connection sheet 22 to the same side. The closer 200 takes the shape of "[". The closure groove channel 111 is located at the side, along the width direction thereof, of the tissue closure device 100.

But in an embodiment where two spaced-apart clamping plates 15 are arranged in each of the first clamping base 11 and the second clamping base 12, the groove channel 111 is the closure groove channel 111. The first closure sheet 21a and the second closure sheet 21b protrude from two opposite ends of the connection sheet 22 to the same side or two sides. The closer 200 takes the shape of "[" or "I". After the closer 200 is assembled with the tissue closure device 100, the connection sheet 22 is located in the groove channel 111.

Further, the distal end of the connection sheet 22 is provided with a first pushing rod 23a and a second pushing rod 23b which protrude towards the distal end. After the closer 200 is assembled with the first clamping base 11 and the second clamping base 12, the first pushing rod 23a and the second pushing rod 23b protrude into the channel 16 of the first clamping base 11 and the channel 16 of the second clamping base 12 respectively. Thus, when the closer 200 moves from the proximal end to the distal end, the first pushing rod 23a and the second pushing rod 23b respectively drive the pushing block 19 of the first clamping base 11 and the pushing block 19 of the second clamping base 12 to move from the proximal end to the distal end.

Further, in order to cut the human tubular tissue while a purse string is formed or after the purse string is formed, the distal end of the connection sheet 22 is designed to be a blade. The connection sheet 22 is a cutting knife blade. The closer 200 is changed to be a cutting knife mechanism. The closure groove channel 111 is a knife feeding groove.

Further, the tissue closure device 100 further comprises a pouch assembly 24 movably connected onto the connection sheet 22. The pouch assembly 24 comprises a staple pusher 242, a pair of needle heads 2411/2412 movably connected onto the staple pusher 242, and a connection portion 2413 connected to the proximal ends of the pair of needle heads 2411/2412. When the staple pusher 242 moves from the proximal end to the distal end, the pair of needle heads 2411/2412 pushes the tubular tissue located in the accommodation cavity 13 to the distal end until the distal ends of the pair of needle heads 2411/2412 are closed to close the tubular tissue into a purse string.

The cutting knife mechanism has an original position at which the blade is located at the proximal ends of the pair of the needle heads 2411/2412 and a firing position at which the blade is located at the distal ends of the pair of needle heads 2411/2412. When the cutting knife mechanism is located at the original position, the pouch assembly 24 and the cutting knife mechanism are at the proximal end of the accommodation cavity 13. When the cutting knife mechanism is located at the firing position, the pouch assembly 24 and the cutting knife mechanism are at the distal end of the accommodation cavity 13. During a process where the cutting knife mechanism moves from the original position to the firing position, after the pouch assembly 24 and the cutting knife mechanism move towards the distal end simultaneously until the pouch assembly 24 closes the tubular tissue into a purse string, the cutting knife mechanism continues to move towards the distal end relative to the purse string so as to cut through the tissue.

In this embodiment, the pair of needle heads 2411/2412 and the connection portion 2413 form a U-shaped thimble 241. The thimble 241 specifically comprises a first needle head 2411, a second needle head 2412 arranged in parallel to the first needle head 2411, and a connection portion 2413 connected to the first needle head 2411 and the second needle head 2412. "Arranged in parallel" refers to that the extending directions of the first needle head 2411 and the second needle head 2412 are substantially parallel and does not specifically refer to being parallel between two straight lines in the strict sense.

In this embodiment, the first needle head 2411 and the second needle head 2412 are slightly staggered in the width direction of the first clamping base 11, so that the first needle head 2411 and the second needle head 2412 are bent in different planes to form a stable purse string, thereby facilitating the use of the circular stapler later.

The staple pusher 242 comprises a staple pushing rod 2421 extending from the proximal end to the distal end and a U-shaped thimble sleeve 2422 located at the distal end of the staple pushing rod 2421. The thimble sleeve 2422 is provided with a hollow portion 2423 open to the distal end for accommodating the connection portion 2413 of the thimble, and partial structures, close to the connection portion 2413, of the first needle head 2411 and the second needle head 2412. The thimble 241 and the thimble sleeve 2422 may be assembled detachably.

When the staple pusher 242 pushes the thimble 241 to move from the proximal end to the distal end, the first needle head 2411 and the second needle head 2412 respectively move in the needle groove 182 of the convex block 18 of the first clamping base 11 and the needle groove 182 of the convex block 18 of the second clamping base 12, pierce into the human tubular tissue, gradually push the human tubular tissue to the distal end and gather the tubular tissue until the distal end, away from the connection portion 2413, of the first needle head 2411 and the distal end, away from the connection portion 2413, of the second needle head 2412 are closed to close the tubular tissue accommodated in the accommodation cavity 13 into a purse string with a gathered center. In this embodiment, the distal end of the first needle head 2411 and the distal end of the second needle head 2412 are respectively bent in the first staple forming groove 1511 and the second staple forming groove 1521 to close the human tubular tissue into a purse string.

Furthermore, the staple pusher 242 is detachably connected to the connection sheet 22 through a fixing element 25. When the staple pusher 242 is fixed to the connection sheet 22, the proximal end of the thimble sleeve 2422 is located at the side, facing the distal end, of the distal end of the connection sheet 22. After the pouch assembly 24 disengages from the cutting knife mechanism, the staple pusher 242 stops moving towards the distal end, and the cutting knife mechanism may continue to move towards the distal end so as to cut the tissue. The staple pushing rod 2421 is provided with a pin hole 2424 at the proximal end, a pin 2425 which may be assembled into the pin hole 2424, and a fixing portion 2426 formed by recessing at the side of the pin hole 2424 which is facing the distal end. The pin hole 2424 and the fixing portion 2426 are arranged at an interval.

In an embodiment where each of the first clamping base 11 and the second clamping base 12 comprises one clamping plate 15, the tissue closure device 100 comprises the pouch assembly 24 located at one side of the groove channel 111. Accordingly, the proximal end of the connection sheet 22 is provided with a fixing sheet 221 protruding towards one side, and a fixing hole 222 which is located at the side of the fixing sheet 221 which is facing the distal end, and penetrates through the connection sheet 22 to accommodate the fixing element 25. A first through hole 251 and a second through hole 2211 which penetrates through in the direction from the proximal end to the distal end for allowing the staple pushing rod 2421 to pass through are arranged on the fixing element 25 and the fixing sheet 221 respectively.

After the staple pushing rod 2421 is assembled with the connection sheet 22, the fixing element 25 is fixed to the fixing portion 2426, the pin 2425 is located in the pin hole 2424 and the connection sheet 22 is clamped between the pin hole 2424 and the fixing element 25.

Further, the staple pushing rod 2421 is further provided with a convex strip 2427 protruding towards the first clamping base 11. The convex strip 2427 extends from the proximal end to the distal end. The section of the staple pushing rod 2421 is of a like-convex shape. The diameter of the fixing portion 2426 is smaller than that of the staple pushing rod 2421, and the diameter of the fixing portion 2426 is smaller than or equal to that of the convex strip 2427. The first through hole 251 has the same section as the staple pushing rod 2421 and comprises a large hole 2511 matched with the staple pushing rod 2421 and a small hole 2512 matched with the convex strip 2427. The staple pushing rod 2421 and the convex strip 2427 may move in the first through hole 251 and the second through hole. The shape of the second through hole 2211 is not specifically required, and the section thereof may be circular. It may be understood by a person skilled in the art that the fixing, portion 2426 may be accommodated in the small hole 2512. The fixing element 25 may be driven to move, in the fixing hole 222, towards the first closure sheet 21a or the second closure sheet 21b.

When the pouch assembly 24 is assembled with the connection sheet 22, the fixing element 25 is placed in the fixing hole 222 firstly, the proximal end of the staple pushing rod 2421 successively passes through the first through hole 251 and the second through hole 2211 from the distal end to the proximal end, and the pin 2425 is inserted into the pin hole 2424. The fixing element 25 is fixed to the fixing portion 2426. The fixing sheet 221 is located between the fixing element 25 and the pin 2425. At this time, the fixing portion 2426 is located in the small hole 2512, and the fixing element 25 is abutted against the convex strip 2427, and thus the fixing element 25 cannot move towards the distal end relative to the staple pushing rod 2421. When the cutting knife mechanism moves towards the distal end, the fixing sheet 221 acts on the fixing element 25, and the fixing element 25 pushes the convex strip 2427, thereby driving the pouch assembly 24 to move from the proximal end to the distal end so as to form a purse string. When the cutting knife mechanism returns from the distal end to the proximal end, the fixing sheet 221 acts on the pin 2425, thereby enabling the pouch assembly 24 to return simultaneously.

The fixing element 25 is further provided with an elastic body 252 which corresponds to the fixing hole 222 and is close to the second closure sheet 21b. The elastic body 252 protrudes towards the second closure sheet 21b. When the fixing element 25 is located in the fixing hole 222, the elastic body 252 is abutted against the side, close to the second closure sheet, in the fixing hole 222. In addition, the fixing element 25 is further provided with a groove 253 which is arranged relative to the elastic body 252 and is close to the first closure sheet 21a. The recessed direction of the groove 253 is consistent with the protruding direction of the elastic body 252, thereby facilitating the assembly of the fixing element 25 and the fixing hole 222.

To be specific, the staple pusher 242 moves from the proximal end to the distal end under the driving of the cutting knife mechanism, and under the action of the elastic body 252, the side surface, located at the proximal end and/or the distal end, of the fixing element 25 is abutted against stepped surfaces of two ends of the fixing portion 2426. At this time, the pouch assembly 24 and the cutting knife mechanism move together towards the distal end. Accordingly, a convex plate 153 protruding towards the first clamping base 11 is arranged at the position on the clamping plate 15 of the second clamping base 12 which is close to the distal end. When the cutting knife mechanism pushes the pouch assembly 24 to move to the distal end and the fixing element 25 reaches the position where the convex plate 153 is located, under the action of the convex plate 153, the action of the elastic body 252 is overcome, and the convex plate 153 is abutted against the fixing element 25, so that the fixing element 25 moves towards the first clamping base 11 in the fixing hole 222, and the fixing portion 2426 disengages from the small hole 2512 and enters the large hole 2511. That is, the large hole 2511 corresponds to the staple pushing rod 2421 and the convex strip 2427 corresponds to the small hole 2512. At the same time, the pushing block 19 is pushed up as being driven by the elastic sheet 161 to move away from the clamping housing 14. That is, the pushing block 19 may be located in a space enclosed by the first pushing rod 23b, the second pushing rod 23a and the connection sheet 22, so that the channel 16 is not occupied, and thus the fixing element 25 and the fixing, sheet 221 may continue to move towards the distal end along the staple pushing rod 2421 so as to enable the cutting knife mechanism to continue to move towards the distal end. At this time, the pouch assembly 24 disengages from the fixing element 25. That is, the pouch assembly 24 stays and the fixing element 25 continues to move towards the distal end. In addition, when the fixing element 25 reaches the position where the convex plate 153 is located, the pushing block 19 is pushed up as being driven by the elastic sheet 161 to move away from the clamping housing 14. As such, the situation that the instrument head cannot easily enter a lower position of the human pelvic floor because the instrument head is too long may be avoided.

The position of the convex plate 153 is arranged as follows: when the fixing element 25 is abutted against the convex plate 153, the thimble 241 of the pouch assembly 24 justly enables the human tubular tissue to form a closed purse string under the action of the first staple forming groove 1511 and the second staple forming groove 1521.

In an embodiment where each of the first clamping base 11 and the second clamping base 12 comprises two clamping plates 15, the tissue closure device 100 comprises two groups of pouch assemblies 24 arranged at two sides of the groove channel 111 respectively. Each of the pouch assemblies 24 corresponds to one clamping plate 15 in the first clamping base 11 and one clamping plate 15 in the second clamping base 12.

Being different from an embodiment where each of the first clamping base 11 and the second clamping base 12 comprises one clamping plate 15, the proximal end of the connection sheet 22 is provided with a fixing sheet 221 protruding towards two sides and a fixing hole 222 which is located at the side, facing the distal end, of the fixing sheet 221 and penetrates through the connection sheet 22 to accommodate the fixing element 25. Two first through holes 251 and two second through holes 2211 which penetrate in the direction from the proximal end to the distal end for allowing the staple pushing rod 2421 to penetrate through are arranged on the fixing element 25 and the fixing sheet 221 respectively. The two first through holes 251 are arranged at two sides of the connection sheet 22 respectively, and the two second through holes 2211 are also arranged at the two sides of the connection sheet 22 respectively. Each of the pouch assemblies 24 is connected to the fixing element 25 and the fixing element 221 which are located at one side of the connection sheet 22. The connection mode thereof is the same as that in the above embodiment and will not be described here.

In another embodiment which is not shown, the connection portion 2413 may also be a purse string line. The distal end of the first clamping base 11 and/or the second clamping base 12 is provided with a closure connector (not shown) cooperating with the pair of needle heads 2411/2412. The closure connector is provided with accommodation holes for accommodating the distal ends of the pair of needle heads 2411/2412. After the needle heads 2411/2412 are connected to the closure connector, the closure connector limits the needle heads 2411/2412 in the axial direction of the pouch assembly 24, and a bundled purse string with a gathered center may be formed by manually tightening the purse string line later. Other structures and the use method thereof are the same as those of the above embodiment and will not be described here.

The using process of the tissue closure device 100 of the present invention is as follows: in the first step, the tissue closure device 100 is assembled with the instrument body and the firing device. Before firing, the cutting knife mechanism is located at the original position. Namely, the cutting knife mechanism is located at the side of the first clamping base 11 which is facing the proximal end. At this time, the first clamping base 11 and the second clamping base 12 may be opened.

In the second step, in the embodiments shown in FIGS. 1-8 combined with FIGS. 16-19, the distal ends of the first clamping base 11 and the second clamping base 12 are separated to open the accommodation cavity 13, part of the human tubular tissue is placed in the accommodation cavity 13, the cutting knife mechanism is pushed to move from the proximal end to the distal end by means of an instrument or manual operation, the first closure sheet 21*a* and the second closure sheet 21*b* act on the first clamping base 11 and the second clamping base 12 respectively, so that the accommodation cavity 13 may be closed, and the part of the human tubular tissue is clamped in the accommodation cavity 13. At this time, the human tubular tissue acts on the convex blocks 18, so that all the convex blocks 18 move towards the clamping housing 14, and thus the tissue closure device 100 may be closed by a relatively small force.

This step, in the embodiments shown in FIGS. 9-15 combined with FIGS. 16-19, slightly differs from the above using process in that: the distal ends of the first clamping base 11 and the second clamping base 12 are separated to open the accommodation cavity 13, the convex block is hidden in the channel under the pressure of the elastic return mechanism 3, part of the human tubular tissue is placed in the accommodation cavity 13, and the cutting knife mechanism may be pushed to move from the proximal end to the distal end by means of an instrument or manual operation with a relatively small force.

In the third step, in the embodiments shown in FIGS. 1-8 combined with FIGS. 16-19, the cutting knife mechanism is driven to move from the proximal end to the distal end, the first pushing rod 23*a* and the second pushing rod 23*b* respectively drive the pushing block 19 in the channel 16 of the first clamping base 11 and the pushing block 19 in the channel 16 of the second clamping base 12 to move from the proximal end to the distal end, the pushing blocks 19 gradually drive the convex blocks 18, from the proximal end to the distal end, to move away from the clamping housing 14, and the convex blocks 18 act on the human tubular tissue to enable the human tubular tissue to be wave-shaped. At the same time, the first needle head 2411 and the second needle head 2412 respectively move in the needle groove 182 of the convex block 18 of the first clamping base 11 and the needle groove 182 of the convex block 18 of the second clamping base seat 12 respectively so as to discontinuously pierce into the human tubular tissue and penetrate through the mucous membrane layer of the human tubular tissue. When the pushing block 19 continues to move towards the distal end, the convex blocks 18 that previously form a wave shape return into the space formed by the clamping plate 15 and the first clamping base 11 as well as the second clamp 12 under the pressure of the tissue due to the loss of the support from the pushing block 19 without hindering the cutting knife mechanism from continuing to move towards the distal end, and the staple pusher 242 pushes the human tissue to move towards the distal end until the human tubular tissue is tied tightly to form a bundled purse string.

Figure 16:
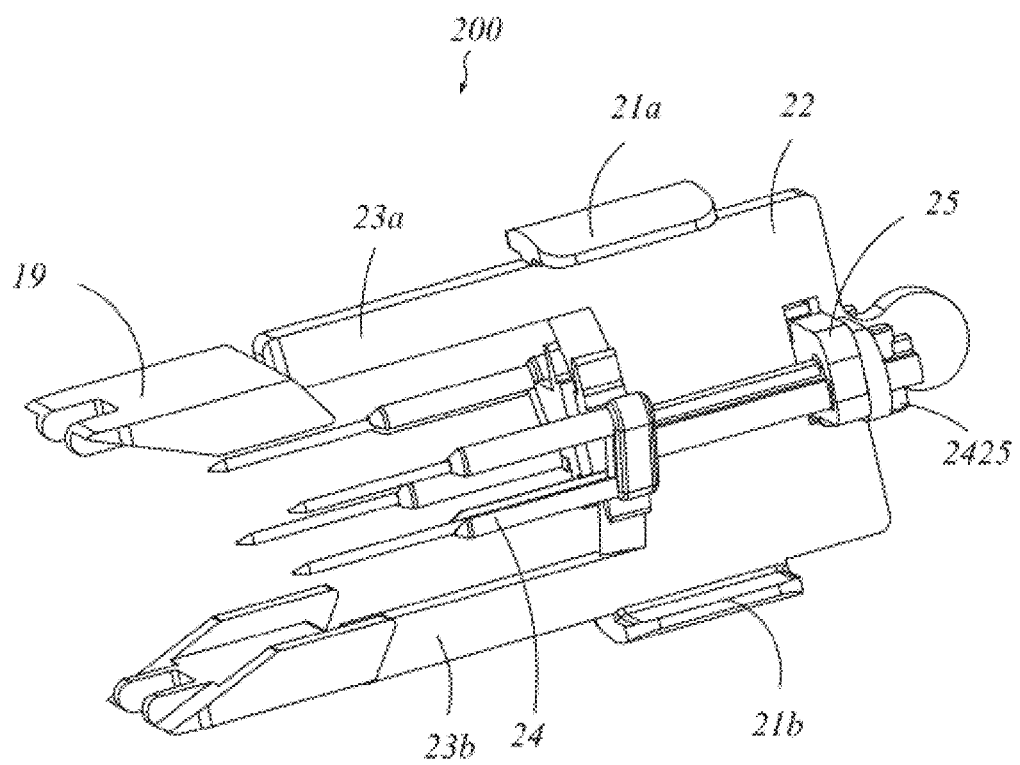
FIG. 16 is a structural diagram when a cutting knife mechanism, a pouch assembly and a pushing block of the present invention cooperate with one another.
Figure 17:
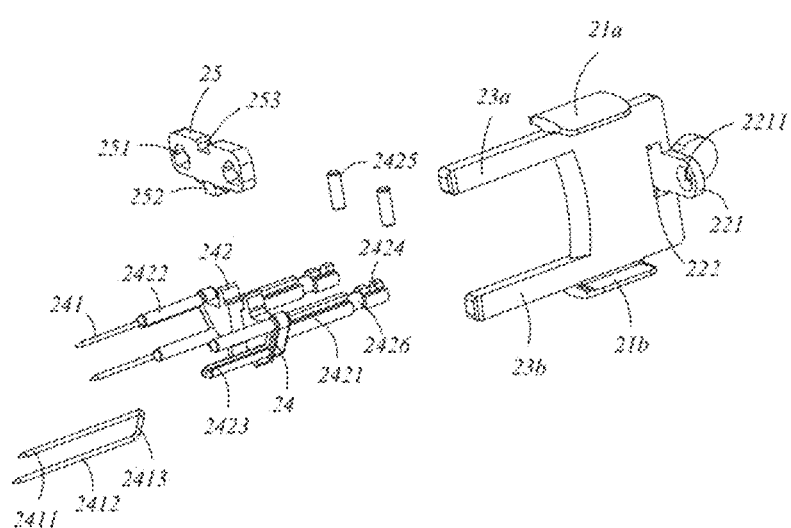
FIG. 17 is an exploded view of the cutting knife mechanism and the pouch assembly shown in FIG. 16.
Figure 18:
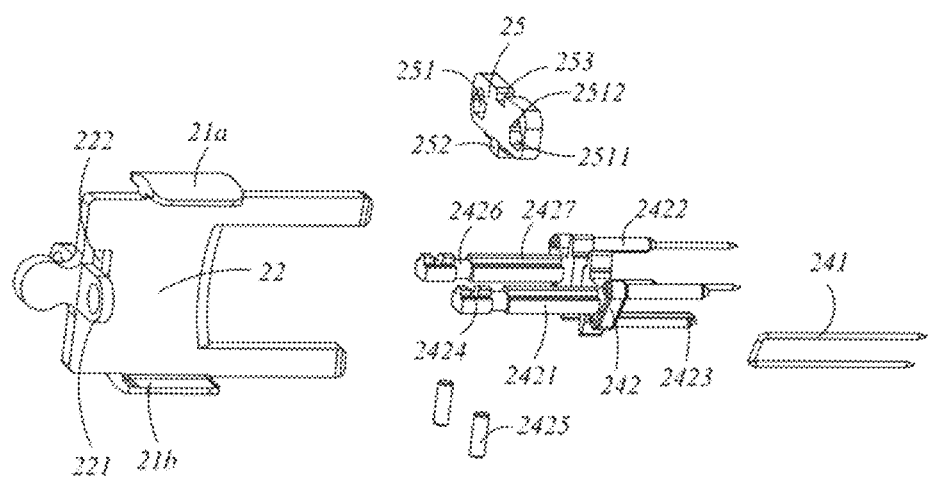
FIG. 18 is an exploded view of the cutting knife mechanism and the pouch assembly shown in FIG. 16 from another perspective.

This step, in the embodiments shown in FIGS. 9-15 combined with FIGS. 16.19, slightly differs from the above using process in that: the pushing block 19 successively drives, from the proximal end to the distal end, the convex blocks 18 to move away from the clamping housing 14, the convex blocks 18 act on the elastic line to enable the elastic line to be in the second state, and at the same time, the convex blocks 18 act on the human tubular tissue to enable the human tubular tissue to be wave-shaped. When the pushing block 19 continues to move towards the distal end, the convex blocks 18 that previously form a wave shape return into the channel 16 formed by the clamping plate 15 and the first clamping base 11 as well as the second clamp 12 under the pressure of the elastic return mechanism 3 due to the loss of the support from the pushing block 19.

In the four step, after the thimble 241 penetrates through the human tubular tissue in the accommodation cavity 13 until the end, away from the connection portion 2413, of the first needle head 2411, and the end, away from the connection portion 2413, of the second needle 2412 respectively reach the first staple forming groove 1511 and the second staple forming groove 1521. The elastic sheet 161 pushes the pushing block 19 to move away from the clamping housing 14 to give way to the first pushing rod 23*a* and the second pushing rod 23*b*, and the cutting knife mechanism continues to move towards the distal end until the first needle head 2411 and the second needle head 2412 are respectively bent in the first staple forming groove 1511 and the second staple forming groove 1521 to close the human tubular tissue into a purse string.

After the purse string is formed, the convex plate 153 acts on the fixing element 25 to enable the fixing element to move towards the first clamping base 11, so that the staple pusher 242 disengages from the connection sheet 22. The cutting knife mechanism continues to move towards the distal end, and the blade cuts off the tubular tissue between the two purse strings.

Finally, the cutting knife mechanism is returned, and the connection sheet 22 acts on the pin 2425, so that the thimble 241 disengages from the thimble sleeve 2422, and the staple pusher 242 and the cutting knife mechanism return to the original position.

In addition, the above pouch assembly 24 may be further used in the first clamping base 11 and the second clamping base 12 without the convex blocks 18. The specific process for only forming a purse string is as follows: the pair of needles 2411/2412 pushes the tubular tissue located in the accommodation cavity 13 to the distal end and gather the tubular tissue between the pair of needles 2411/2412 and the connection portion 2413 until the distal ends of the pair of needles 2411/2412 are closed to close the tubular tissue into a purse string. Other structures and the use method thereof are the same as those of the above embodiment and will not be described here.

To sum up, according to the tissue closure device 100 of the present invention, the convex block 18 is driven to move towards or away from the clamping housing 14 by the pushing block 19 and the elastic return mechanism 3 to enable the clamped human tubular tissue to be wave-shaped, so that the thimble 241 may discontinuously penetrate through the human tubular tissue, the formed purse string may penetrate through the mucous membrane layer of the human tubular tissue and is not easy to slide off. In addition, in the present invention, by means of the cutting knife mechanism, the closure of the first clamping base 11 and the second clamping base 12, the pushing of the pushing block 19 to move from the proximal end to the distal end in the channel 16, the formation of the purse string for the human tubular tissue and the cutting of the human tubular tissue may be realized comprehensively, which is simple to operate and convenient to use and reduces the surgery costs.

It should be understood that although the description is described with embodiments, not every embodiment includes only one independent technical solution. This statement of the description is only for clarity. Those skilled in the art should consider the description as a whole, and the technical solutions in all of the embodiments may also be properly combined to form other embodiments that will be understood by those skilled in the art.

The above detailed description only aims to specifically illustrate the feasible embodiments of the present invention, and is not intended to limit the scope of protection of the present invention. Equivalent embodiments or modifications thereof made without departing from the spirit of the present invention shall fall within the scope of protection of the present invention.

The invention claimed is:

1. A tissue closure device comprising:
a first clamping base and a second clamping base configured to be opened and closed relatively and form an accommodation cavity after being closed, wherein:
each of the first clamping base and the second clamping base comprises a clamping housing, a clamping plate fixed in the clamping housing, and a channel located between the clamping housing and the clamping plate and extending from a proximal end to a distal end of the clamping plates of the first clamping base and the second clamping base;
each of the clamping plates of the first clamping base and the second clamping base is provided with a plurality of openings arranged at intervals from the proximal end to the distal end and configured to communicate with a corresponding channel and the accommodation cavity, and a plurality of convex blocks located in the openings respectively and configured to get close to or apart from each of the clamping housings of the first clamping base and the second clamping base in the openings in the direction perpendicular to each of the clamping plates;
a needle groove configured to penetrate through the plurality of convex blocks from the proximal end to the distal end and communicate with the accommodation cavity is arranged on the plurality of convex blocks; and
the plurality of convex blocks on the clamping plates of the first clamping base and the second clamping base are staggered from the proximal end to the distal end;
a pushing block configured to be driven to move from the proximal end to the distal end in each of the channels to successively drive the plurality of convex blocks on each of the clamping plates to move in the direction away from the clamping housing, wherein after the pushing block moves towards the distal end, a convex block of the plurality of convex blocks located at a proximal end of the pushing block is configured to disengage from the pushing block; and
a pouch assembly configured to be driven to move from the proximal end to the distal end of the clamping plates of the first clamping base and the second clamping base comprises a staple pusher, a pair of needle heads movably connected to the staple pusher, and a connection portion connected to proximal ends of the pair of needle heads, wherein when the staple pusher moves from the proximal end to the distal end of the clamping plates of the first clamping base and the second clamping base, the pair of needle heads are configured to respectively move in the needle grooves of the plurality of convex blocks on the clamping plates of the first clamping base and the second clamping base, pierce into a tubular tissue, gradually push the tubular tissue to the distal end of the clamping plates of the first clamping base and the second clamping base and gather the tubular tissue until the distal ends of the pair of the needle heads are closed to close the tubular tissue into a purse string.

2. The tissue closure device according to claim 1, wherein the pair of needle heads and the connection portion form a U-shaped thimble; a first buckling block protruding towards the second clamping base is arranged at the distal end of the clamping plate of the first clamping base, and a first staple forming groove corresponding to the needle groove of the convex block on the clamping plate of the first clamping base is arranged on the first buckling block; and a second buckling block protruding towards the first clamping base is arranged at the distal end of the clamping plate of the second clamping base, and a second staple forming groove corresponding to the needle groove of the convex block on the clamping plate the second clamping base is arranged on the second buckling block.

3. The tissue closure device according to claim 1, wherein at least one directional column is arranged on one of the openings and the convex block; a directional groove matched with the directional column is arranged on the other one of the openings and the convex block; and the directional column cooperates with the directional groove to guide the convex block to move close to or away from the clamping housing.

4. The tissue closure device according to claim 1, wherein a side of each of the convex blocks, facing the clamping housing, is provided with an inclined plane located at the proximal end and a plane located at the distal end of the inclined plane; and the pushing block is provided with an inclined plane portion which is located at the distal end and cooperates with the inclined plane, and a plane portion located at the proximal end of the inclined plane portion.

5. The tissue closure device according to claim 4, wherein the width of the plane portion along the direction from the proximal end to the distal end is greater than the width of the convex block along the direction from the proximal end to the distal end.

6. The tissue closure device according to claim 1, further comprising an elastic sheet located at the distal end of each of the channels to drive the pushing block to move in the direction away from the clamping housing, wherein after the pushing block moves towards the distal end, the convex block located at the proximal end of the pushing block disengages from the pushing block.

7. The tissue closure device according to claim 1, further comprising an elastic return mechanism, and the elastic return mechanism is an elastic line, wherein along the direction perpendicular to the clamping plate, two ends of the elastic return mechanism are cooperatively arranged on the convex block and the clamping plate respectively; when the pushing block drives the elastic return mechanism to move towards the direction away from the clamping housing, the elastic return mechanism elastically deforms; and when the convex block disengages from the pushing block, the elastic return mechanism acts on the convex block to enable the convex block to be located in the channel.

8. The tissue closure device according to claim 1, wherein each of the plurality of convex blocks comprises a first wall and a second wall which are opposite and arranged at an interval, and a connection wall connected to the first wall and the second wall; and the first wall, the second wall and the connection wall define the needle groove which is open towards a side away from the connection wall.

9. The tissue closure device according to claim 8, wherein an inner wall surface of the first wall which is located in the needle groove, is parallel to an outer wall surface of the first wall which is away from the needle groove; an outer wall surface of the second wall which is away from the needle groove, is parallel to the outer wall surface of the first wall; and an inner wall surface of the second wall which is located in the needle groove, is gradually inclined, from the connection wall to the side away from the connection wall and towards a direction away from the first wall.

10. The tissue closure device according to claim 1, wherein a closure groove channel extending from the proximal end to the distal end is arranged on each of the first clamping base and the second clamping base; the tissue closure device further comprises a cutting knife mechanism; the cutting knife mechanism comprises a first closure sheet located at a side of the first clamping base which is away from the second clamping base, a second closure sheet located at a side of the second clamping base which is away from the first clamping base, and a connection sheet connected to the first closure sheet and the second closure sheet in the closure groove channel; the distal end of the connection sheet is a blade;

the cutting knife mechanism has an original position at which the blade is located at the proximal ends of the pair of the needle heads and a firing position at which the blade is located at the distal ends of the pair of needle heads; when the cutting knife mechanism is located at the original position, the pouch assembly and the cutting knife mechanism are at the proximal end of the accommodation cavity; when the cutting knife mechanism is located at the firing position, the pouch assembly and the cutting knife mechanism are at the distal end of the accommodation cavity; and during a process where the cutting knife mechanism moves from the original position to the firing position, after the pouch assembly and the cutting knife mechanism move towards the distal end simultaneously until the pouch assembly closes the tubular tissue into a purse string, the cutting knife mechanism continues to move towards the distal end relative to the purse string to cut through the tissue.

11. The tissue closure device according to claim 10, wherein the first closure sheet and the second closure sheet protrude from two opposite ends of the connection sheet to at least one side of the connection sheet; a closure mechanism takes the shape of "[" or "I"; the tissue closure device comprises two groups of pouch assemblies arranged at two sides of the closure groove channel respectively, each of the staple pushers comprises a staple pushing rod extending from the proximal end to the distal end, and a thimble sleeve located at the distal end of the staple pushing rod to accommodate the needle heads and the connection portion; and the staple pushing rod and the connection sheet are movably connected through a fixing element; and the connection sheet configured to be driven to move along the length direction of the staple pushing rod.

12. The tissue closure device according to claim 11, wherein the staple pushing rod is provided with a pin hole at the proximal end, a pin configured to be assembled into the pin hole and a fixing portion formed by recessing at a side of the pin hole which is facing the distal end, and the pin hole and the fixing portion are arranged at an interval; the proximal end of the connection sheet is provided with a fixing sheet protruding towards two sides and a fixing hole which is located at a side of the fixing sheet which is facing the distal end, and penetrates through the connection sheet to accommodate the fixing element; two first through holes and two second through holes which penetrate in the direction from the proximal end to the distal end for allowing the staple pushing rod to penetrate through are arranged on the fixing element and the fixing sheet respectively; the two first through holes are arranged at two sides of the connection sheet respectively, and when the fixing element is located in the fixing hole, the two second through holes are arranged at the two sides of the connection sheet respectively; and after the staple pushing rod is assembled with the fixing element and the fixing sheet which are located at one side of the connection sheet, the fixing portion is located in a first through hole of the fixing element, the pin is located in the pin hole, and the connection sheet is clamped between the pin hole and the fixing element.

13. The tissue closure device according to claim 12, wherein the staple pushing rod is further provided with a convex strip protruding towards the first closure sheet, and the convex strip extends from the proximal end to the distal end; a size of the fixing portion is smaller than a size of the staple pushing rod, and is smaller than or equal to a size of the convex strip; each of the two first through holes comprises a large hole matched with the staple pushing rod and a small hole matched with the convex strip, and the large hole is configured to communicate with the small hole; a convex plate protruding towards the first clamping base is arranged at a position on the second clamping base which is close to the distal end, to drive the fixing element to move towards the first closure sheet or the second closure sheet in the fixing hole; and the fixing element is further provided with an elastic body which corresponds to the fixing hole and is close to the second closure sheet.

14. The tissue closure device according to claim 10, wherein the cutting knife mechanism further comprises a first pushing rod and a second pushing rod which protrude from the distal end of the connection sheet towards the distal end; and the first pushing rod and the second pushing rod respectively push the pushing blocks to move from the proximal end to the distal end in the channels of the first clamping base and of the second clamping base.

15. A medical instrument comprising an instrument body, a tissue closure device detachably connected to a distal end of the instrument body, and a firing device connected to the instrument body for triggering the tissue closure device, wherein the tissue closure device is the tissue closure device according to claim 1.

\* \* \* \* \*